(12) United States Patent
Ouchi et al.

(10) Patent No.: US 6,554,850 B1
(45) Date of Patent: *Apr. 29, 2003

(54) ENDOSCOPIC BIOPSY FORCEPS

(75) Inventors: Teruo Ouchi, Saitama (JP); Masaru Nagamine, Kagawa (JP)

(73) Assignee: Pentax Corporation, Tokyo (JP)

( * ) Notice: Subject to any disclaimer, the term of this patent is extended or adjusted under 35 U.S.C. 154(b) by 126 days.

This patent is subject to a terminal disclaimer.

(21) Appl. No.: 09/654,521

(22) Filed: Sep. 1, 2000

(30) Foreign Application Priority Data

| Sep. 3, 1999 | (JP) | ............................................ 11-250068 |
| Sep. 8, 1999 | (JP) | ............................................ 11-253931 |
| Sep. 9, 1999 | (JP) | ............................................ 11-255146 |

(51) Int. Cl.[7] .............................................. A61B 17/44
(52) U.S. Cl. ..................................................... 606/205
(58) Field of Search ................................ 606/205, 208, 606/167, 170, 1, 207, 127, 206; 600/564, 562, 104, 300, 101

(56) References Cited

U.S. PATENT DOCUMENTS

| 4,690,175 A | * | 9/1987 | Ouchi et al. ................. 138/131 |
| 5,810,876 A | * | 9/1998 | Kelleher ....................... 606/205 |
| 5,947,979 A | * | 9/1999 | Ouchi et al. ................. 606/113 |
| 6,013,095 A | * | 1/2000 | Ouchi .......................... 606/205 |
| 6,074,408 A | * | 6/2000 | Freeman ...................... 606/205 |
| 6,106,543 A | * | 8/2000 | Esser .......................... 606/205 |
| 6,206,904 B1 | * | 3/2001 | Ouchi .......................... 606/207 |
| 6,283,924 B1 | * | 9/2001 | Ouchi .......................... 600/564 |
| 6,299,630 B1 | * | 10/2001 | Yamamoto ................... 606/205 |
| 6,378,351 B1 | * | 4/2002 | Ouchi et al. ................... 72/336 |
| 6,402,738 B1 | * | 6/2002 | Ouchi ............................ 606/1 |
| 6,402,773 B1 | * | 6/2002 | Ouchi .......................... 606/205 |

* cited by examiner

Primary Examiner—John J. Calvert
Assistant Examiner—Alissa L. Hoey
(74) Attorney, Agent, or Firm—Greenblum & Bernstein, P.L.C.

(57) ABSTRACT

Endoscopic biopsy forceps that allow for smooth action of drive levers to ensure that forceps cups formed integral with the drive levers will positively open and close. Parallel grooves are formed in the drive levers in a direction perpendicular to the longitudinal axis of a support shaft and connecting members for coupling a manipulating wire and the drive levers are coupled to the drive levers within the parallel grooves.

24 Claims, 13 Drawing Sheets

ENDOSCOPIC BIOPSY FORCEPS

BACKGROUND OF THE INVENTION

The present invention relates to endoscopic biopsy forceps that is passed through the forceps channel in an endoscope to collect a tissue specimen for biopsy from within a body cavity.

Endoscopic biopsy forceps generally comprises two integral assemblies of forceps cups and drive levers. The two integral assemblies of forceps cups and drive levers are provided at the distal end of a sheath. A manipulating wire extending through the sheath is moved back and forth along the longitudinal axis so that the drive levers pivot about a support shaft and the forceps cups are driven to open and close like beaks.

FIG. 16 shows a typical coupling structure for the drive lever and the manipulating wire in endoscopic biopsy forceps of this type. The distal end of a manipulating wire (not shown) is connected to a link plate 13 arranged parallel to a drive lever 8 and interposed between the manipulating wire and the drive lever. The link plate 13 is rotatably connected to the drive leber 8 by a rivet 18. Shown by 7 in FIG. 16 is a forceps cup.

Since the drive lever 8 and the link plate 13 are connected together in a "cantilever" manner by the rivet 18, wear, rattles and other phenomenon that occur during use may often cause them to come out of the parallel state as shown in FIG. 17. Consequently, the rivet 18 either skews or otherwise deforms to prevent smooth movement of the driver lever 8 and the link plate 13. In the worst case, the rivet 18 may come off.

The integral assembly of forceps cups and drive levers has heretofore been formed by cutting stainless bars and the like. However, in view of its extremely high cost, the assembly is currently formed by subjecting a plate material to press working (see Unexamined Published Japanese Patent Application (kokai) Nos. 276285/1997 and 24045/1998).

FIG. 18 shows an example of an integral assembly of a forceps cup 7 and a driver lever 8, which is produced by press working. FIG. 19 is a sectional view of the boundary 9 between the forceps cup 7 and the drive lever 8. As shown in FIGS. 18 and 19, the drive lever 8 and the boundary 9 are formed by bending a metal plate material so that one half of the plate material is closely contacted with the other half of the plate material When a pair of forceps cups 7 are allowed to bite a mucosal membrane tissue of a living body, a large force acts on the forceps cups 7 in random directions and the concentrated stress works on the boundary 9 which is the neck of each forceps cup 7.

Since the boundary 9 which is formed by bending the metal plate material so that one half of the plate material is closely contacted with the other half of the plate material is vulnerable to lateral bending forces and, hence, the boundary 9 bends laterally in the direction indicated by arrow A in FIG. 18, often causing the forceps 7 to deform as if they have swiveled laterally.

SUMMARY OF THE INVENTION

An object, therefore, of the present invention is to provide endoscopic biopsy forceps that allow for smooth action of the drive levers to ensure that the forceps cups formed integral with them will positively open and close.

Endoscopic biopsy forceps according to a first aspect of the present invention comprises a sheath, two integral assemblies of forceps cups and drive levers that are provided at a distal end of the sheath and a manipulating wire extending through the sheath which is moved back and forth along a longitudinal axis so that the drive levers pivot about a support shaft and the forceps cups are driven to open and close like beaks. Parallel grooves are formed respectively in the drive levers in a direction perpendicular to a longitudinal axis of the support shaft. Connecting members for coupling the manipulating wire and the drive levers are coupled to the drive levers within the parallel grooves.

Preferably, each of the drive levers retains the two ends of an associated pin-shaped member extending across the parallel groove in a vertical direction, and the connecting members are plate-shaped link members each coupled pivotally to the respective pin-shaped member. Alternatively, the connecting members may be wire-shaped members each coupled pivotally to the respective pin-shaped member.

In another preferred embodiment, a through-hole is pierced in that part of the wall of each of the drive levers which faces the parallel groove, the connecting members are wire-shaped members extending through the respective through-holes, and a removal preventive member too large to pass through the through-hole is engaged with the distal end portion of each of the wire-shaped members. Alternatively, the wire-shaped members may each be formed of the distal end portion of the manipulating wire.

If desired, the forceps cups and the drive levers maybe formed of a plate material by press working. The drive levers may be formed in a generally U-shaped cross section.

Endoscopic biopsy forceps according to a second aspect of the present invention comprises a sheath, two integral assemblies of forceps cups and drive levers that are provided at a distal end of the sheath and a manipulating wire extending through the sheath which is moved back and forth along a longitudinal axis so that the drive levers pivot about a support shaft and the forceps cups are driven to open and close like beaks. A wire-shaped member provided at the tip of the manipulating wire is bent back to form a loop, and the material of which the drive levers are made forms a wire engaging portion at the distal end of each drive lever so that the loops of the wire-shaped member are brought into rotatable engagement with the wire engaging portions of the drive levers.

If desired, the forceps cups and the drive levers may be formed of a plate by press working, and the distal end portion of each wire engaging portion may be formed in a cylindrical round shape that centers on a longitudinal axis parallel to the support shaft and which is loosely fitted into the associated wire loop.

The wire engaging portions may be formed in such a way that the material of which the drive levers are formed is partially superposed on itself. Alternatively, the wire-shaped member may be formed of the distal end portion of the manipulating wire itself.

Another object of the invention is to provide durable endoscopic biopsy forceps that can be manufactured at low cost by forming integral assemblies of forceps cuss and drive levers by press working and which yet is resistant to lateral bending and subsequent deformation in the boundary between each forceps cups and the associated drive lever.

Endoscopic biopsy forceps according to a third aspect of the present invention comprises a sheath, two integral assemblies of forceps cups and drive levers that are formed by press working and which are provided at the distal end of the sheath and a manipulating wire extending through the sheath which is moved back and forth along a longitudinal axis so that the drive levers pivot about a support shaft and the forceps cups are driven to open and close like beaks. The boundary between each forceps cup and the associated drive lever is formed in a generally U-shaped cross section.

If desired, a hole through which the support shaft is passed is formed near the boundary between each forceps cup and the associated drive lever. Each drive lever may be formed as a part continuous to the boundary which has a generally U-shaped cross section.

The present disclosure relates to the subject matter contained in Japanese patent application Nos. Hei. 11-250068 (filed on Sep. 3, 1999), 11-253931 (filed on Sep. 8, 1999) and 11-255146 (filed on Sep. 9, 1999)), which are expressly incorporated herein by reference in their entireties.

DESCRIPTION OF THE PREFERRED EMBODIMENT

Preferred embodiments of the invention are described below with reference to accompanying drawings.

Figure 1:
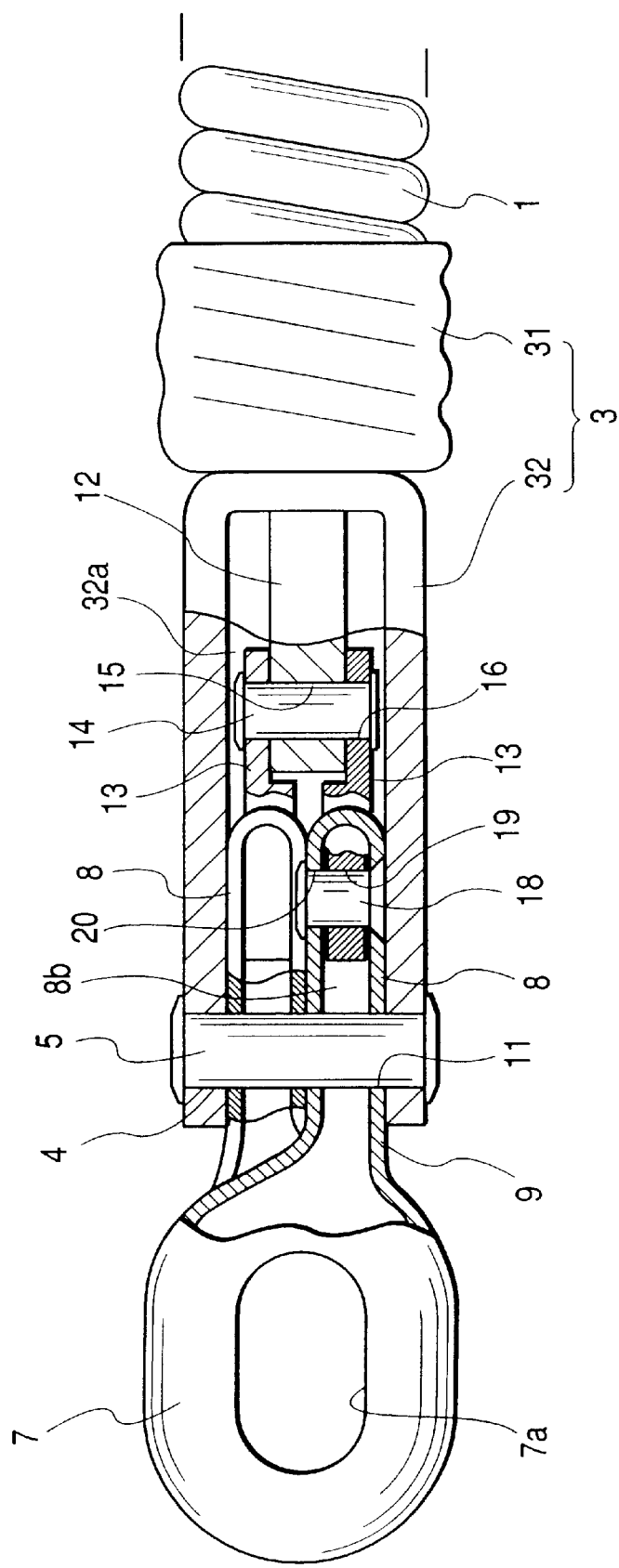
FIG. 1 is a plan view showing different sections of the tip portion of endoscopic biopsy forceps in a closed state according to a first embodiment of the invention.
Figure 2:
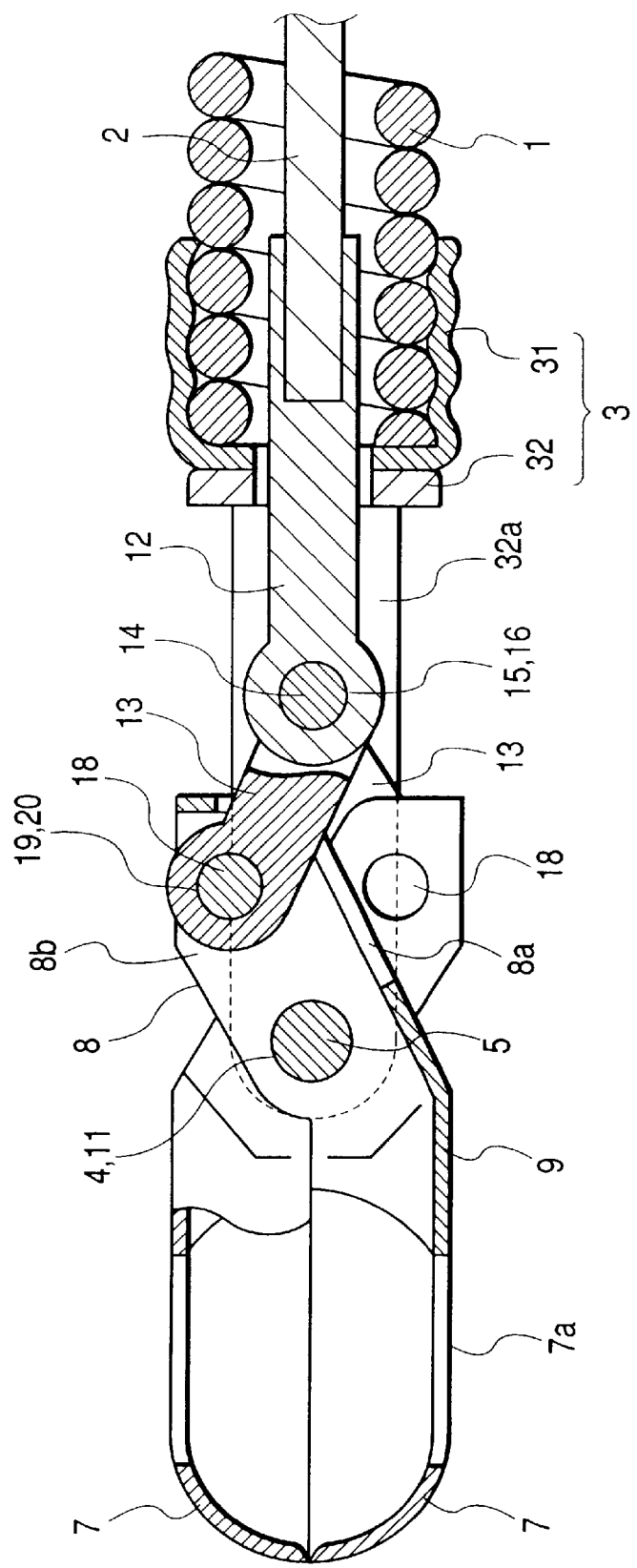
FIG. 2 is a side view showing different sections of the tip portion of endoscopic biopsy forceps in a closed state according to the first embodiment of the invention.

FIGS. 1 and 2 show the distal end portion of endoscopic biopsy forceps according to the first embodiment of the invention; FIG. 1 is a plan view with part shown in section and FIG. 2 is a side view with part shown in section. Note that either figure shows different sections at the same time in order to save space.

Indicated by numeral 1 is a flexible sheath that is inserted into or removed from the forceps channel in an endoscope (not shown) and which is made up of a coil pipe that is formed of a stainless steel wire wound in close turns in a specified diameter.

The sheath 1 may have a flexible tube fitted over the coil pipe or it may have other suitable constructions. The sheath is typically about 1–2.5 m in length, and about 1.5–3 mm in diameter.

A manipulating wire 2 extends through the entire length of the sheath 1 and it can be moved back and forth along the longitudinal axis by control with a manipulating section (not shown) coupled to the basal end of the sheath 1.

A support assembly 3 is securely coupled to the distal end of the sheath 1. This assembly includes an annular connector 31 coupled to the distal end of the sheath 1, and a U-shaped support frame 32 secured to its distal end.

In the embodiment under consideration, the annular connector 31 is a cap-shaped member having spiral ridges on the surface that engage the periphery of the distal end of the sheath 1. The support frame 32 is a U-shaped plate member that is open in the front portion and which has a rear end portion secured to the annular connector 31. A through-hole is formed along the center line of the connection between the annular connector 31 and the support frame 32 in such a way that a wire coupling link 12 to be described later can be loosely fitted through the hole.

A support shaft receiving hole 4 is pierced through the support assembly 3 in an area near its distal end (near the distal end of the support frame 32 to be more exact) in a direction perpendicular to the longitudinal axis. A support shaft 5 is passed through the hole 4 and fixed in position by crimping both ends.

Two integral assemblies, each having a forceps cup 7 and a drive lever 8, are rotatably supported on the shaft 5. A pair of forceps cups 7 are disposed to project forward from the support assembly 3, with their open sides facing each other.

Figure 3:
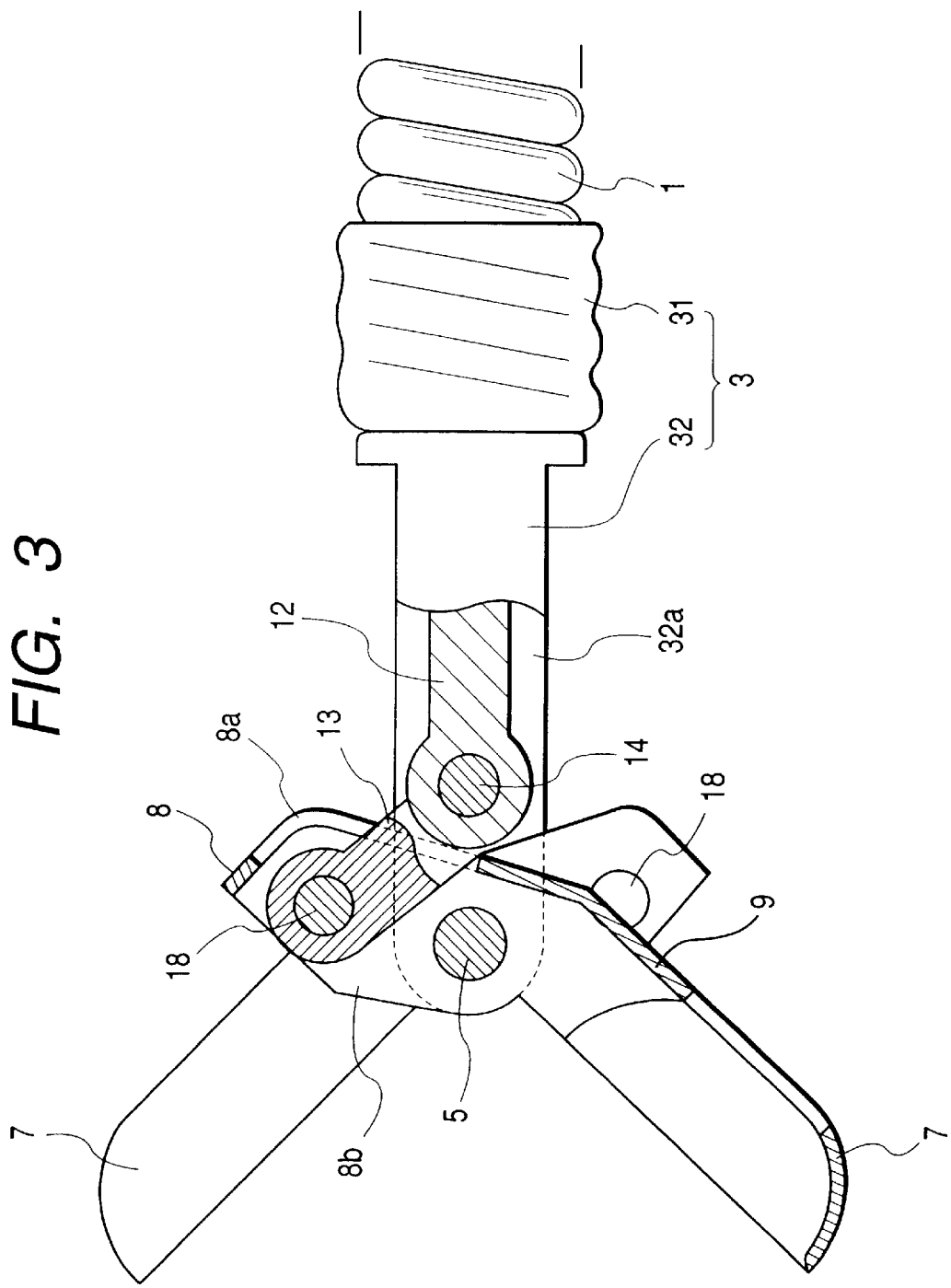
FIG. 3 is a plan view showing different sections of the tip portion of endoscopic biopsy forceps in an open state according to the first embodiment of the invention.

The drive levers 8 are movably accommodated within the opening 32a of the U-shaped support frame 32. The support shaft 5 having the two ends retained by the support assembly 3 is passed through a shaft hole 11 pierced in each of the drive levers 8. When the drive levers 8 pivot about the shaft 5, the forceps cups 7 which are formed integral with the respective drive levers 8 open and close like beaks. FIG. 3 shows the forceps cups 7 in an open state.

Figure 4:
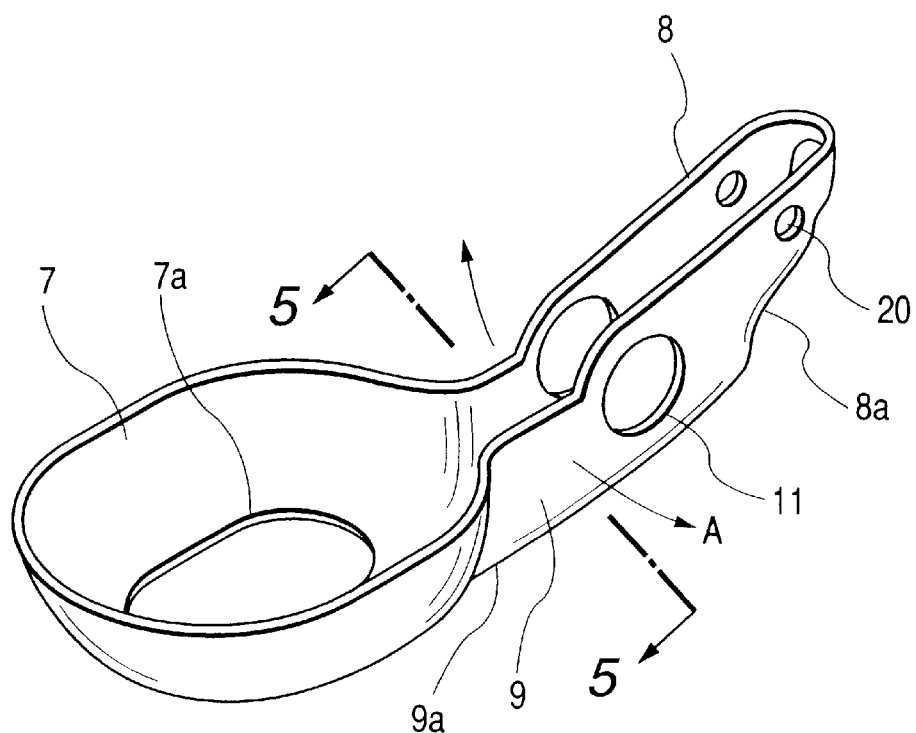
FIG. 4 is a perspective view of a member which is an integral combination of a forceps cup and a drive lever in the endoscopic biopsy forceps according to the first embodiment of the invention.

The integral assembly of forceps cup 7 and the drive lever 8 is formed of a single stainless plate by press working. FIG. 4 is a perspective view of the integral assembly of forceps cup and driver lever. A plane view of the assembly is shown, partly in section, in FIG. 1.

The assembly of forceps cup 7 and drive lever 8 has a general shape resembling a spoon with a short handle. Each of the forceps cups 7 is shaped like an oval bowl having a hole 7a in the back and a blade along the edge of the open side.

Figure 5:
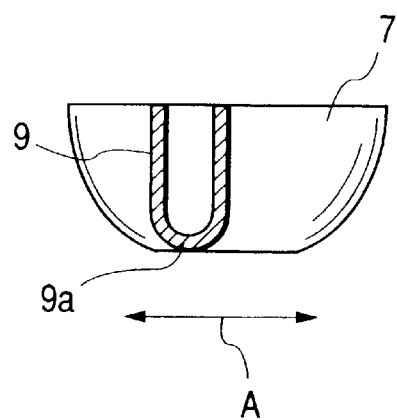
FIG. 5 is section 5—5 of FIG. 4 showing the boundary between the forceps cup and the drive lever in the endoscopic biopsy forceps according to the first embodiment of the invention.

FIG. 5 is section 5—5 of the boundary 9 between the forceps cup 7 and the drive lever 8. As shown, the boundary 9 has a generally U-shaped cross section and the drive lever 8 also has a generally U-shaped cross section continuous to the boundary 9. This portion having a generally U-shaped cross section has high strength since its bottom works as a beam counteracting a lateral force.

Thus, the boundary 9 is not formed by simply bending and superposing a plate, but it is formed into a generally U-shaped cross section, so the bottom 9a of the boundary 9 works as a beam counteracting a lateral force A to have a sufficient strength against deformation due to such lateral force A. In FIG. 5, the bottom 9a of the boundary 9 is formed in a semicircular shape but, if desired, the bottom 9a may be shaped linearly.

A rod of wire connecting link 12 is secured to the distal end of the manipulating wire 2 such that fits distal end portion is located within the opening 32a of the support assembly 3. The distal end portion of the wire connecting link 12 is held between two link plates 13 which are pivotally coupled together by a rivet 14 such that they can pivot on a point near the distal end of the wire connecting link 12.

The rivet 14 is loosely and rotatably fitted through a hole 15 in the wire connecting link 12 and its two ends are retained by holes 16 made in the two link plates 13 and crimped.

The generally U-shaped drive levers 8 have hollow spaces 8b which form parallel grooves extending normal to the longitudinal axis of the support shaft 5. The other end of each link plate 13 is inserted into the associated groove 8b, and the link plate 13 is pivotally coupled to the mating drive lever 8 by a rivet 18 (pin-shaped member) the two ends of which are retained by the drive lever 8.

The two rivets 18 are loosely and rotatably fitted into holes 19 made in the respective link plates 13, and the two ends of each rivet are retained in holes 20 made in each drive lever 8. Shown by 8a is a slot formed in the bottom of each drive lever 8 to permit the passage of the associated link plate 13.

Thus, the two link plates 13 and the two drive levers 8 make up a pantograph-shaped link mechanism. As the manipulating wire 2 is moved back and forth by the operator, the wire connecting link 12 and the link plates 13 cause the drive levers 8 to pivot about the support shaft 5 so that the forceps cups 7 open and close like beaks.

Since the link plates 13 are fitted in parallel grooves 8b in the drive levers 8 and engaged with the rivets 18 each being received at the two ends by the associated drive levers, the link plates 13 and the drive levers 8 do not lean or skew at their joints but move smoothly to ensure that the forceps cups 7 open and close in a positive manner.

As the forceps cups 7 close, they hold a portion of the mucosal tissue of a living body with a strong bite and tear it off, leaving a specimen of the tissue within the cups. Even if a strong lateral force works on the boundary 9 which is the neck of each forceps cup 7, the generally U-shaped boundary 9 has a sufficient strength against deformation due to lateral forces.

The present invention is by no means limited to the foregoing embodiment and various modifications may be adopted. For instance, the forceps cups 7 may take on any other shapes such as an alligator clip, or link plates 13 as the mechanism for opening and closing the forceps cups 7 may be substituted by wires or any other means.

Figure 6:
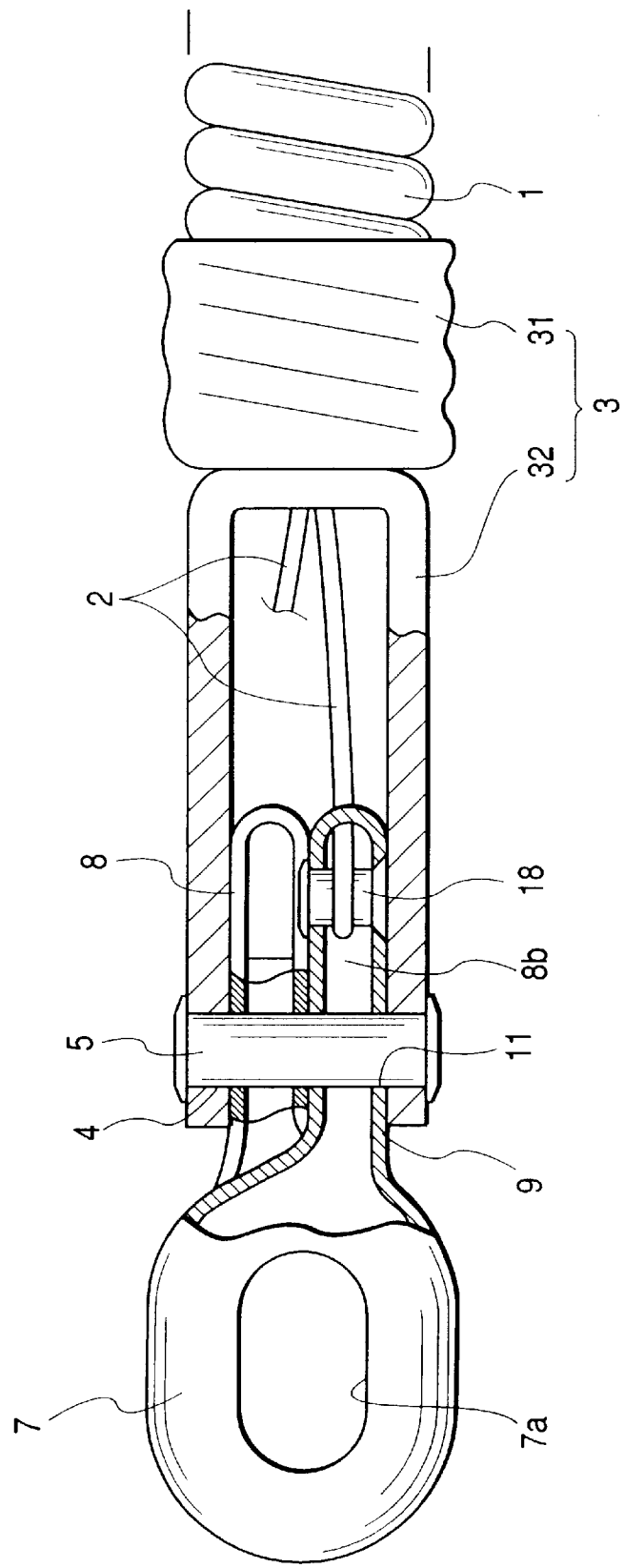
FIG. 6 is a plan view showing different sections of the tip portion of endoscopic biopsy forceps in a closed state according to a second embodiment of the invention.
Figure 7:
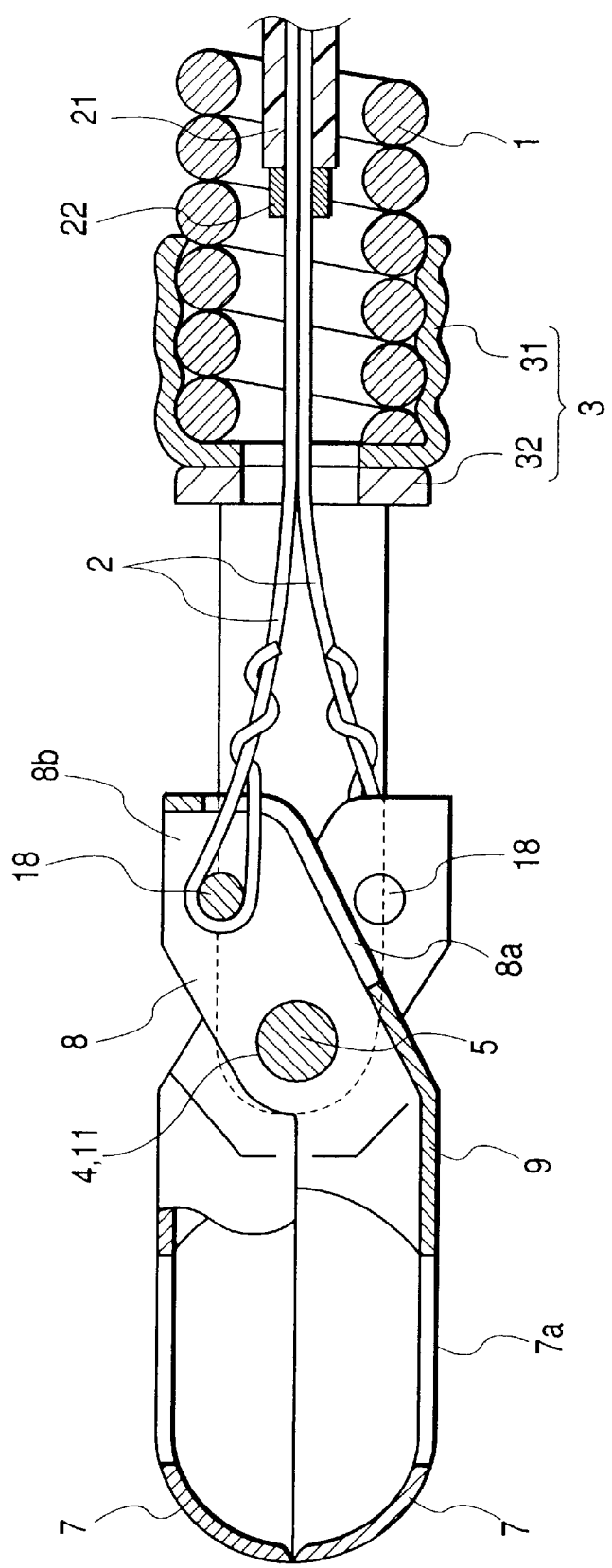
FIG. 7 is a side view showing different sections of the tip portion of endoscopic biopsy forceps in a closed state according to the second embodiment of the invention.

FIGS. 6 and 7 show the tip portion of endoscopic biopsy forceps according to a second embodiment of the invention. FIG. 6 is a plan view with part shown in section and FIG. 7 is a side view with part shown in section. Note that either figure shows different sections at the same time in order to save space.

In the second embodiment, wire-shaped members are substituted for the wire coupling link 12 and the link plates 13 that are used in the first embodiment. The two manipulating wires 2 placed side by side are bent back at the distal end to form loops, into which the rivets 18 are rotatably passed.

As the manipulating wires 2 are moved back and forth, the drive levers 8 are driven to open and close the forceps cups. 7. Since the distal ends of the manipulating wires are engaged with the rivets 18 each being retained at the two ends by the associated drive lever 8, the manipulating wires 2 and the drive levers 8 do not lean or skew at their joints but move smoothly to ensure that the forceps cups 7 open and close in a positive manner.

The two manipulating wires 2 extending through the sheath 1 are placed side by side in contact with each other as they are encased by a single flexible tube 21 which is typically made of a polytetrafluoroethylene resin. In order to ensure that they will not be displaced in position from each other, the two manipulating wires 2 are fixed together by a securing ring 22 near the tip of the flexible tube 21.

Figure 8:
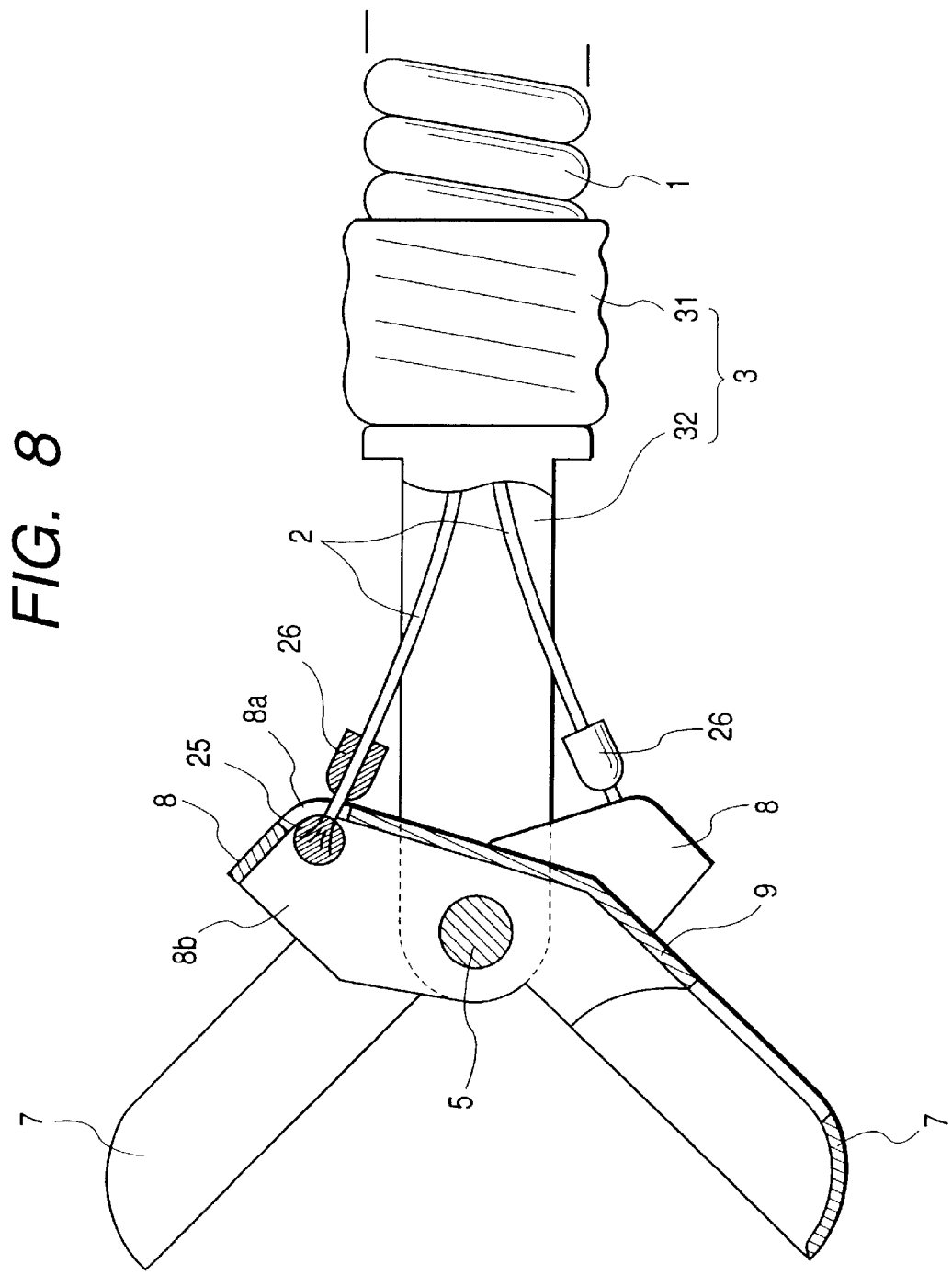
FIG. 8 is a side view showing different sections of the tip portion of endoscopic biopsy forceps in an open state according to a third embodiment of the invention.

FIG. 8 shows the tip portion of endoscopic biopsy forceps according to a third embodiment of the invention. As in the second embodiment, the distal end portions of the two manipulating wires 2 are coupled to the drive levers 8.

The difference is that the rivets 18 are eliminated and that removal preventive members 25 and 26 are used. The removal preventive members 25 and 26 are too large to pass through the slot 8a formed in the bottom wall of each drive lever 8. The removal preventive members 25 and 26 are secured to the associated manipulating wire 2 at two points near its distal end, one being within the drive lever 8 and the other outside it.

In this embodiment, the slots 8a, facing the parallel grooves 8b in the generally U-shaped drive levers 8, are formed along the center lines through the bottoms of the drive levers 8 in a minimum length that is shorter than in the first and second embodiments and which will not interfere with the manipulating wires 2.

As the manipulating wires 2 are moved back and forth, the drive levers 8 are driven to open and close the forceps cups 7. Since the distal ends of the manipulating wires 2 are engaged with the drive levers 8 along their center lines, the manipulating wires 2 and the drive levers 8 do not lean or skew at their joints but move smoothly to ensure that the forceps cups 7 open and close in a positive manner.

The invention is by no means limited to he three embodiments described above and the forceps cups 7 may take on any other shapes such as an alligator tip.

FIGS. 9 to 13 show a fourth embodiment of the present invention.

In the embodiment under consideration, the two manipulating wires 2 extending through the sheath 1 are placed side by side as they are encased by a single flexible tube 21 which is typically made of a polytetrafluoroethylene resin. In order to ensure that they will not be displaced in position from each other, the two manipulating wires 2 are fixed together by means of a securing ring 22 near the tip of the flexible tube 21.

Each of the two manipulating wires 2 is bent back at the tip to form a closed loop 2a which is engaged with a wire engaging portion 18 formed at the rear end of the associated drive lever 8.

Figure 9:
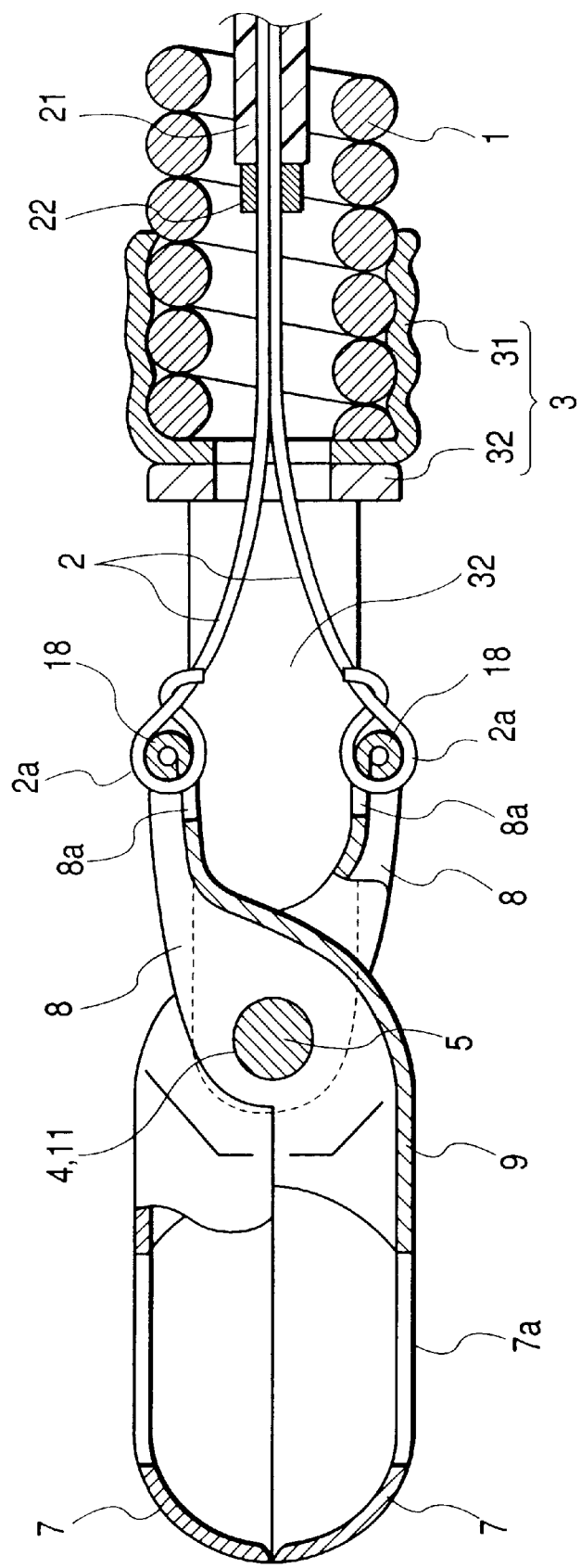
FIG. 9 is a side view showing different sections of the tip portion of endoscopic biopsy forceps in a closed state according to a fourth embodiment of the invention.
Figure 10:
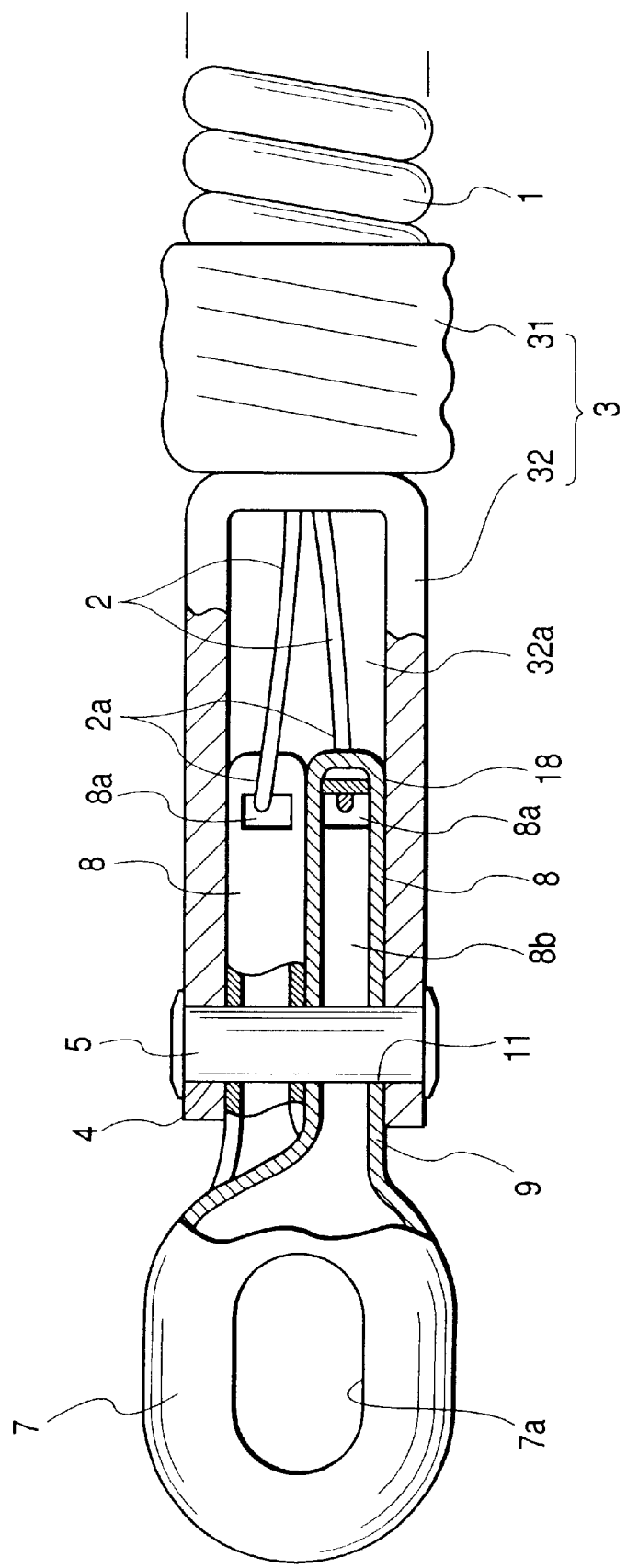
FIG. 10 is a plan view showing different sections of the tip portion of endoscopic biopsy forceps in a closed state according to the fourth embodiment of the invention.
Figure 11:
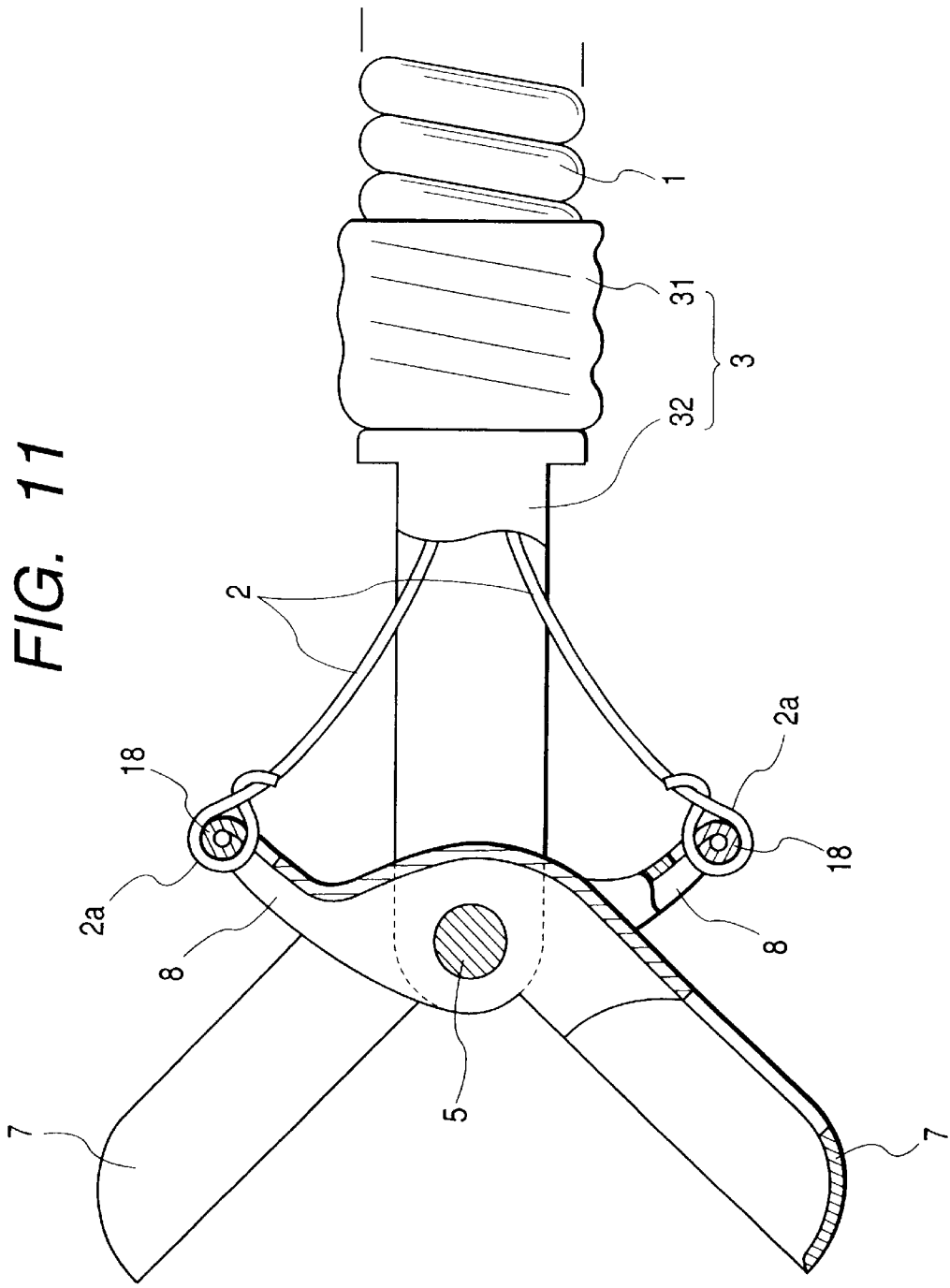
FIG. 11 is a plan view showing different sections of the tip portion of endoscopic biopsy forceps in an open state according to the fourth embodiment of the invention.
Figure 12:
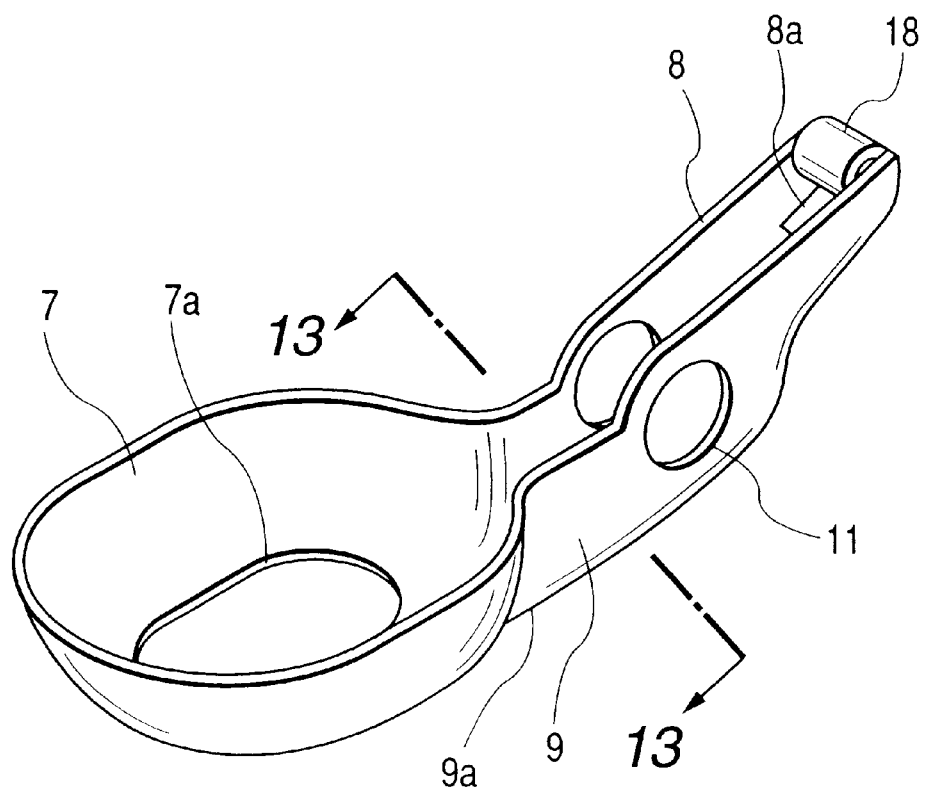
FIG. 12 is a perspective view of a member which is an integral combination of a forceps cup and a drive lever in the endoscopic biopsy forceps according to the fourth embodiment of the invention.
Figure 13:
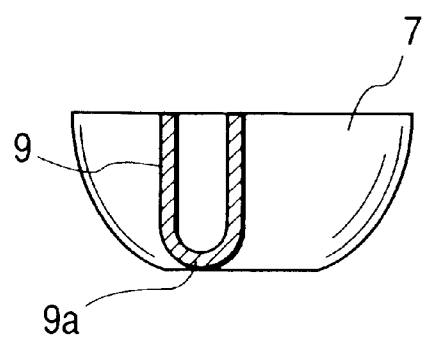
FIG. 13 is section 13—13 of FIG. 12 showing the boundary between the forceps cup and the drive lever in the endoscopic biopsy forceps according to the fourth embodiment of the invention.

The wire engaging portion 18 is a cylindrical round part of the rear end of the drive lever 8 that is formed to have a longitudinal axis parallel to the support shaft 5. The loop 2a of each manipulating wire 2 is loosely fitted around the wire engaging portion 18 in such a way that it can rotate about the latter. As shown in FIG. 9, the wire engaging portions 18 are spaced apart by a distance substantially equal to the outside diameter of the sheath 1 and positioned ahead of it.

Figure 14:
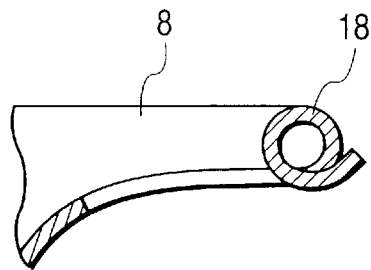
FIG. 14 is partial section showing a modification of a wire engaging portion in the endoscopic biopsy forceps according to the fourth embodiment of the invention.
Figure 15:
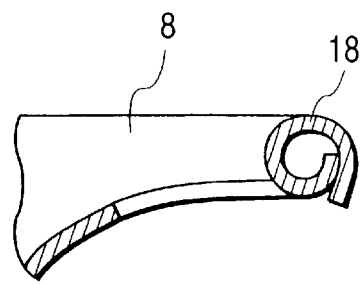
FIG. 15 is partial section showing another modification of a wire engaging portion in the endoscopic biopsy forceps according to the fourth embodiment of the invention.
Figure 16:
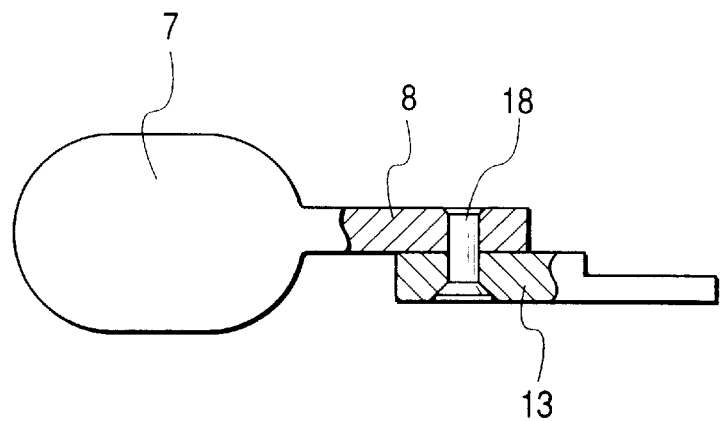
FIG. 16 is a plan view of related endoscopic biopsy forceps with part shown in section.
Figure 17:
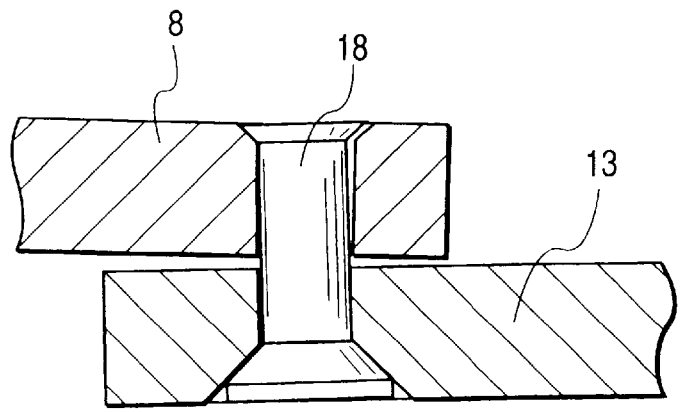
FIG. 17 is a partially enlarged sectional view of the related endoscopic biopsy forceps.
Figure 18:
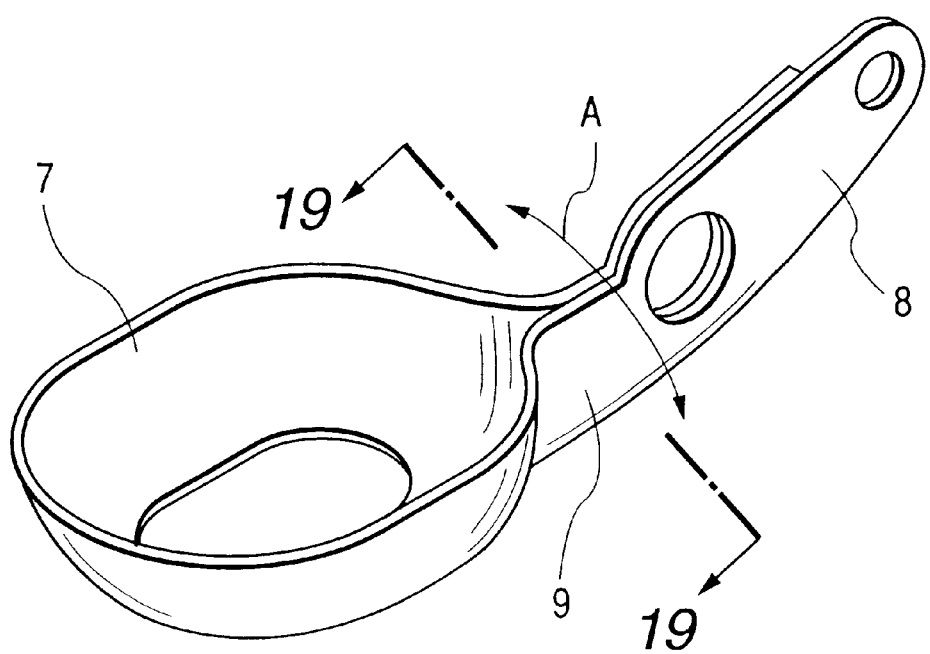
FIG. 18 is a perspective view of a member which is an integral combination of a forceps cup and a drive lever in the related endoscopic biopsy forceps.
Figure 19:
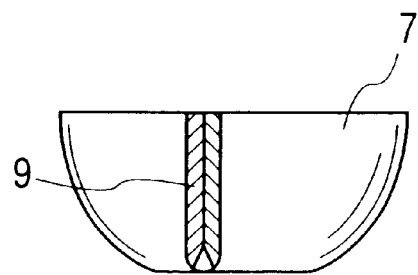
FIG. 19 is section 19—19 of FIG. 18 showing the boundary between the forceps cup and the drive lever in the related endoscopic biopsy forceps.

Each drive lever 8 has a slot 8a formed in the bottom in an area adjacent the wire engaging portion 18 and the loop 2a of the manipulating wire 2 is passed through the slot. The wire engaging portion 18 may be formed from a wall of a drive lever 8, which is largely cutout from the drive lever 8 and partly rolled over itself as shown in FIGS. 14 and 15

As the manipulating wires 2 are moved back and forth by the operator, the drive levers 8 rotate about the support shaft 5 so that the forceps cups 7 open and close like beaks. As the forceps cups 7 close, they hold a portion of the mucosal tissue of a living tissue with a strong bite and tear it off, leaving a specimen of the tissue within the cups.

Since the wire engaging portions 18 are spaced apart from each other by a distance generally equal to the outside diameter of the sheath 1 (i.e., they are located away off the central axis to a certain degree) and positioned ahead of the latter, the pulling of the manipulating wires 2 causes the forceps cups 7 to have a sufficiently strong closing force that the mucosal tissue can be efficiently torn off.

Since the distal end portion of each manipulating wire 2 is engaged with the rear end portion of the associated drive lever 8 substantially along the center line of the drive lever 8 having the generally U-shaped cross section, the drive levers 8 do not lean or skew but move smoothly to ensure that the forceps cups 7 open and close in a positive manner.

The present invention is by no means limited to the foregoing embodiments, and various modifications can be made. For instance, the manipulating wire 2 that is engaged with the rear end of the associated drive lever 8 may be a separate member coupled to the distal end of the manipulating wire 2 extending through the sheath 1, and the forceps cups 7 may take on any other shapes such as an alligator clip.

According to the invention, parallel grooves are formed in the drive levers in a direction perpendicular to the longitudinal axis of the support shaft and the connecting members for coupling the manipulating wire and the drive levers are coupled to the drive levers within the parallel grooves. As a result, the drive levers formed integral with forceps cups do not lean or skew at the joints to the connecting members but move smoothly to ensure that the forceps cups will open and close in a positive way.

According to the invention, forceps cups and drive levers are formed integral by press working, so endoscopic biopsy forceps can be manufactured at low cost. What is more, the boundary between each forceps cup and the associated drive lever is formed in a generally U-shaped cross section and has sufficient resistance against lateral bending and subsequent deformation, thus providing high durability for the forceps.

According to the invention, the wire-shaped member provided at the tip of the manipulating wire is bent back to form a loop, which is brought into engagement with the wire engaging portion that is formed at the rear end of each drive lever and which is made of the same material as the drive levers. In consequence, the drive levers formed integral with the forceps cups do not lean or skew but move smoothly to ensure that the forceps cups open and close in a positive manner to produce an effective closing force.

What is claimed is:

1. An integral assembly of a forceps cup and a drive lever, which is to be disposed at a distal end of endoscopic biopsy forceps, the integral assembly comprising:

a cup part forming the forceps cup;

a pair of side walls extending from the cup part substantially in parallel to each other to form the drive lever, the side walls being spaced from each other to define a groove therebetween;

a bottom wall extending from the cup part, and connecting the side walls together to define a bottom of the groove; and a slot formed through the bottom wall, and located opposite from the cup part.

2. The integral assembly according to claim 1, wherein each of the side walls has a first through-hole located at a boundary between the forceps cup and the drive lever.

3. The integral assembly according to claim 2, wherein each of the side walls has a second through-hole located opposite from the cup part with respect to the boundary.

4. The integral assembly according to claim 3, further comprising:

a discrete rivet having two ends supported respectively by the side walls through the second through-holes, wherein an intermediate portion of the rivet between the two ends is located within the groove and confronted with the slot.

5. The integral assembly according to claim 2, further comprising;

a cylindrical engaging portion at a rear end portion of the drive lever, the engaging portion being at least partially located within the groove.

6. The integral assembly according to claim 5, wherein the engaging portion is formed by rolling a part of the bottom wall.

7. The integral assembly according to claim 6, wherein the slot is formed as a consequence of rolling the part of the bottom wall.

8. The integral assembly according to claim 1, wherein the bottom wall is semicircular in section.

9. The integral assembly according to claim 1, wherein the bottom wall is substantially linearly in section.

10. Endoscopic biopsy forceps comprising:

a sheath;, two integral assemblies of forceps cups and drive levers that are provided at a distal end of the sheath; and a manipulating wire extending through the sheath which is moved back and forth along a longitudinal axis of the sheath so that the drive levers pivot about a support shaft and the forceps cups are driven to open and close like beaks, wherein parallel grooves are formed respectively in the drive levers in a direction perpendicular to a longitudinal axis of the support shaft; and wherein connecting members for coupling the manipulating wire and the drive levers are coupled respectively to the drive levers within the parallel grooves.

11. The endoscopic biopsy forceps according to claim 10, wherein each of the drive levers retains two ends of an associated pin-shaped member extending across the parallel groove in a vertical direction, and the connecting members include plate-shaped link members coupled pivotally to the respective pin-shaped members.

12. The endoscopic biopsy forceps according to claim 10, wherein each of the drive levers retains two ends of an associated pin-shaped member extending across the parallel groove in a vertical direction, the connecting members include wire-shaped members coupled pivotally to the respective pin-shaped members.

13. The endoscopic biopsy forceps according to claim 10, wherein a through-hole is pierced in that part of a wall of each drive levers which faces the parallel groove, the connecting members include wire-shaped members passing through the respective through-holes, and a removal preventive member too large to pass through the through-hole is retained on a distal end portion of each of the wire-shaped members.

14. The endoscopic biopsy forceps according to claim 12, wherein a distal end portion of the manipulating wire forms the wire-shaped members.

15. The endoscopic biopsy forceps according to claim 13, wherein a distal end portion of the manipulating wire forms the wire-shaped members.

16. The endoscopic biopsy forceps according to claim 10, wherein the forceps cup and the drive lever of the integral assembly is formed by subjecting a plate material to press working.

17. The endoscopic biopsy forceps according to claim 10, wherein each of the drive levers is substantially U-shaped in cross section.

18. Endoscopic biopsy forceps comprising:

a sheath;

two integral assemblies of forceps cups and drive levers that are provided at a distal end of the sheath; and a manipulating wire extending through the sheath which is moved back and forth along a longitudinal axis so that the drive levers pivot about a support shaft and the forceps cups are driven to open and close like beaks, wherein wire-shaped members provided at a distal end of the manipulating wire are bent back to form loops, respectively, wherein wire engaging portions are formed at rear end portion of the drive levers by integral parts of the drive levers, respectively, and wherein the loops of the wire-shaped members are brought into rotatable engagement with the wire engaging portions of the drive levers, respectively.

19. The endoscopic biopsy forceps according to claim 18, wherein the forceps cup and the drive lever of the integral assembly is formed by subjecting a plate to press working, and the rear end portion of the wire engaging portion is formed into a cylindrical round shape that centers on an axis parallel to the support shaft and which is loosely fitted into the associated wire loop.

20. The endoscopic biopsy forceps according to claim 19, wherein the wire engaging portion is formed in such a way that the integral part forming the drive lever is partially superposed on itself.

21. The endoscopic biopsy forceps according to claim 18, wherein a distal end portion of the manipulating wire forms the wire-shaped members.

22. Endoscopic biopsy forceps comprising:

a sheath;

two integral assemblies of forceps cups and drive levers that are formed by press working and which are provided at the distal end of the sheath; and a manipulating wire extending through the sheath which is moved back and forth along a longitudinal axis of the sheath so that the drive levers pivot about a support shaft and the forceps cups are driven to open and close like beaks, wherein a boundary between each forceps cup and the associated drive lever is formed in a generally U-shaped cross section.

23. The endoscopic biopsy forceps according to claim 22, wherein a hole through which the support shaft is passed is formed near the boundary between each forceps cup and the associated drive lever.

24. The endoscopic biopsy forceps according to claim 22, wherein each drive lever is formed in a-generally U-shaped cross section continuous from the boundary.

* * * * *